United States Patent
Imai et al.

(10) Patent No.: US 8,170,493 B2
(45) Date of Patent: May 1, 2012

(54) TRANSMISSION DEVICE, AND WIRELESS COMMUNICATION APPARATUS USING THE SAME

(75) Inventors: Norio Imai, Ehime (JP); Akiyoshi Oozawa, Ehime (JP)

(73) Assignee: Panasonic Corporation, Osaka (JP)

( * ) Notice: Subject to any disclaimer, the term of this patent is extended or adjusted under 35 U.S.C. 154(b) by 310 days.

(21) Appl. No.: 12/594,990

(22) PCT Filed: Dec. 12, 2008

(86) PCT No.: PCT/JP2008/003754
§ 371 (c)(1),
(2), (4) Date: Oct. 7, 2009

(87) PCT Pub. No.: WO2009/081536
PCT Pub. Date: Jul. 2, 2009

(65) Prior Publication Data
US 2010/0120374 A1 May 13, 2010

(30) Foreign Application Priority Data
Dec. 20, 2007 (JP) .................................. 2007-328366

(51) Int. Cl.
*H04B 1/00* (2006.01)
(52) U.S. Cl. .......................................... 455/68; 600/365
(58) Field of Classification Search .................. 600/365; 455/68, 39, 69–70, 73, 82–88, 91–92, 103, 455/115.1
See application file for complete search history.

(56) References Cited

U.S. PATENT DOCUMENTS
| | | | |
|---|---|---|---|
| 2004/0116786 A1 | 6/2004 | Iijima et al. | |
| 2005/0228313 A1* | 10/2005 | Kaler et al. | 600/583 |
| 2006/0194564 A1 | 8/2006 | Hokimoto et al. | |

FOREIGN PATENT DOCUMENTS
| | | | |
|---|---|---|---|
| CA | 2 450 054 | | 5/2004 |
| EP | 1 422 677 | | 5/2004 |
| JP | 2001-309428 | | 11/2001 |
| JP | 2001-309428 A | * | 11/2001 |
| JP | 2002-251461 | | 9/2002 |
| JP | 2003-208685 | | 7/2003 |
| JP | 2004-234622 | | 8/2004 |
| JP | 2005-176165 | | 6/2005 |
| JP | 2005-341436 | | 12/2005 |
| JP | 2005-341436 A | * | 12/2005 |
| WO | 2005/013637 | | 2/2005 |

OTHER PUBLICATIONS

International Search Report issued Mar. 10, 2009 in International (PCT) Application No. PCT/JP2008/003754.

* cited by examiner

*Primary Examiner* — Nay A Maung
*Assistant Examiner* — Angelica Perez
(74) *Attorney, Agent, or Firm* — Wenderoth Lind & Ponack, L.L.P.

(57) ABSTRACT

A transmission device includes a transmitter for transmitting various signals to a reception device, a receiver for receiving a response signal emitted from the reception device in response to the transmission of the various signals from the transmitter to the reception device, a transmission/reception controller for performing control of the receiver and the transmitter, and a reception specifier for specifying the reception timing of the intermittent reception of the reception device when a response signal from the reception device has been received. The transmission/reception controller decides the timing at which the transmission of the various signals will begin, and how long the transmission will last, on the basis of the reception timing specified by the reception specifier.

9 Claims, 7 Drawing Sheets

TRANSMISSION DEVICE, AND WIRELESS COMMUNICATION APPARATUS USING THE SAME

BACKGROUND

1. Technical Field

The present invention relates to a transmission device that performs communication with respect to reception device that performs intermittent reception, and to a wireless communication apparatus in which this transmission device is used.

2. Background Art

For example, a wireless communication apparatus may comprise a measurement apparatus (transmission device) such as a blood glucose meter or a manometer, and a portable information terminal (reception device) for acquiring information about the above by wireless communication. In this case, the portable information terminal sends the measurement data measured with the measurement apparatus to a data processing apparatus at a medical facility or the like by utilizing a communications network (see Patent Citation 1, for example).

With a wireless communication apparatus such as this, a technique has been disclosed with which reception is performed intermittently in order to reduce power consumption during communication (see Patent Citation 2, for example).

Patent Citation 1: Japanese Laid-Open Patent Application 2002-251461
Patent Citation 2: Japanese Laid-Open Patent Application 2003-208685

SUMMARY

However, the following problems are encountered with the technology disclosed in the above publications.

Specifically, since communication needs to be matched to the intermittent reception operation of the reception device, a problem is that the transmission device takes longer to transmit, so the power consumption of the transmission device rises.

In view of this, it is an object of the present invention to provide a transmission device with which power consumption can be reduced, and a wireless communication apparatus in which this transmission device is used.

To achieve this object, the transmission device of the present invention is a transmission device for performing communication with a reception device that performs intermittent reception, comprising a transmitter, a receiver, a reception specifier, and a transmission/reception controller. The transmitter transmits various signals to the reception device. The receiver receives a response signal emitted from the reception device in response to the transmission of the various signals from this transmitter to the reception device. The reception specifier specifies the reception timing of the intermittent reception of the reception device when a response signal from the reception device has been received. The transmission/reception controller performs control of the receiver and the transmitter and decides the timing at which the transmission of the various signals will begin, and how long the transmission will last, on the basis of the reception timing specified by the reception specifier.

The wireless communication apparatus of the present invention comprises the above-mentioned transmission device and a reception device. The reception device sends a response signal to the transmission device upon properly receiving the various signals transmitted from this transmission device.

Figure 1:
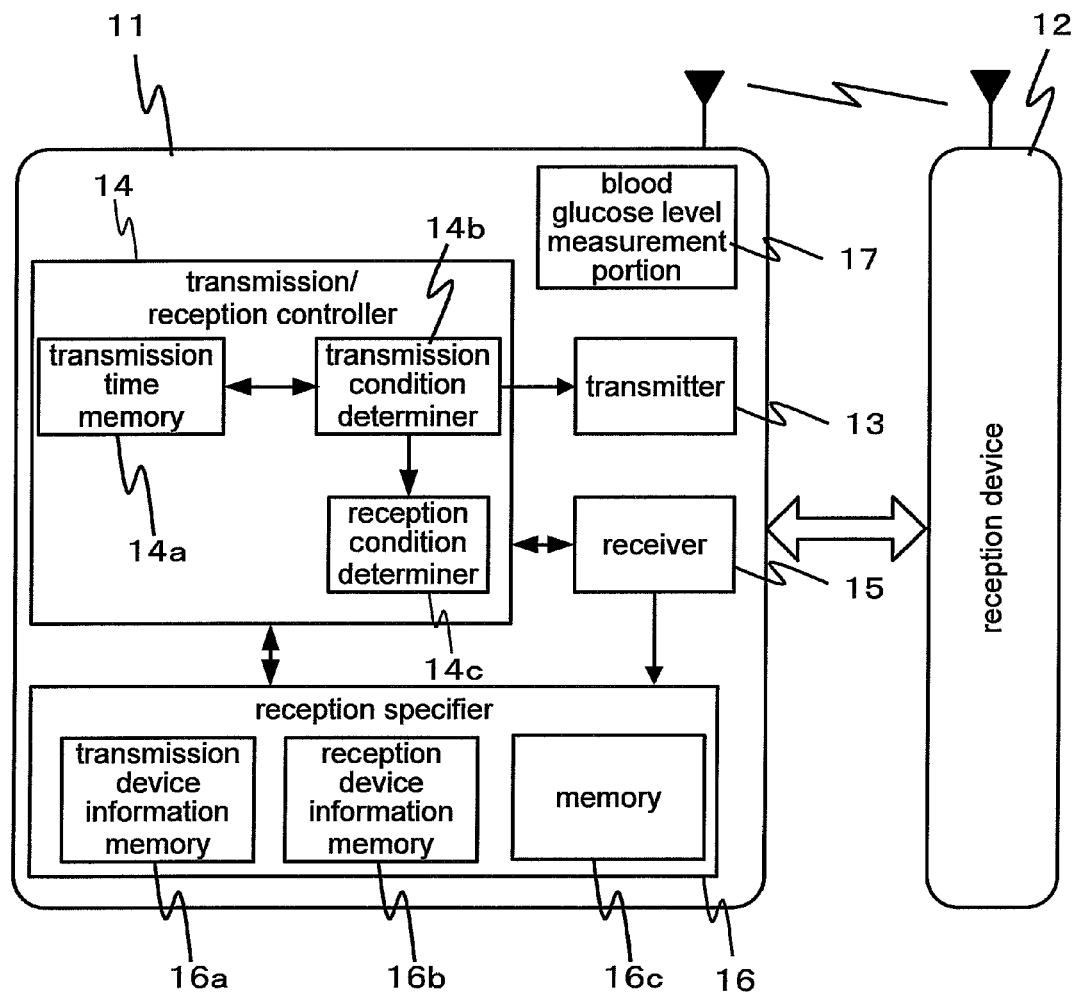
FIG. 1 is a diagram of the configuration of a wireless communication apparatus in Embodiment 1.

EXPLANATION OF REFERENCE 11 transmission device
12 reception device
13 transmitter
14 transmission/reception controller
14a transmission time memory
14b transmission condition determiner
14c reception condition determiner
15 receiver
16 reception specifier
16a transmission device information memory
16b reception device information memory
16c memory
17 blood glucose level measurement portion
21 actuation signal transmission operation
22 response signal reception operation
23 data transmission operation
24 transmission start timing of actuation signal
25 transmission duration of actuation signal
26 reception duration of response signal
27 data transmission waiting time from acknowledge signal reception until start of data transmission
28 data transmission duration
29 intermittent reception operation
30 intermittent reception duration
31 intermittent reception interval
32 response signal transmission waiting time
33 response signal transmission operation
34 data reception operation
35 intermittent reception resumption waiting time
36, 53 intermittent reception timing
37 actuation signal pulse
51 actuation signal transmission start timing
52 actuation signal transmission duration 54 response signal reception duration
55 response signal transmission start timing
56 response signal reception start timing

DETAILED DESCRIPTION

Embodiments of the transmission device of the present invention, and of the wireless communication apparatus in which this transmission device is used, will now be described in detail through reference to the drawings.

Embodiment 1

FIG. 1 is a diagram of the configuration of a wireless communication apparatus in this embodiment.

As shown in FIG. 1, the wireless communication apparatus is constituted so as to include a transmission device 11 and a reception device 12. In the example given here, the transmission device 11 is a wireless blood glucose meter that measures a blood glucose level and performs wireless communication, while the reception device 12 is a wireless communication apparatus that is a portable information terminal that stores measured blood glucose levels and displays them on a graph, or sends them through a network to a medical facility or the like.

The transmission device 11 comprises a transmitter 13, a transmission/reception controller 14, a receiver 15, a reception specifier 16, and a blood glucose level measurement portion 17. The transmitter 13 sends an actuation signal and data to the reception device 12. The transmission/reception controller 14 controls the receiver and controls the transmission of actuation signal (various signals) and data (various signals). The receiver 15 receives response signals from the reception device 12. The reception specifier 16 specifies the reception timing of the intermittent reception of the reception device 12 when the response signal is an acknowledge signal (response signal) that is a notification of the completion of reception from the reception device 12. The blood glucose level measurement portion 17 measures blood glucose levels.

An example will be given here in which the transmission device 11 and the reception device 12 operate as follows.

Specifically, after an actuation signal has been sent from the transmission device 11 to the reception device 12 that is performing intermittent reception, an acknowledge signal is returned from the reception device 12. The transmission device 11 and reception device 12 are then synchronized, after which data is sent from the transmission device 11 to the reception device 12. When the transmission of data is complete, the reception device 12 resumes intermittent reception.

The transmission/reception controller 14 comprises a transmission time memory 14a, a transmission condition determiner 14b, and a reception condition determiner 14c. The transmission time memory 14a stores the time at which the actuation signals are sent. The transmission condition determiner 14b decides the timing at which the actuation signals are sent and the transmission duration. The reception condition determiner 14c decides the reception operation conditions for receiving acknowledge signals by the receiver 15.

The reception specifier 16 comprises the transmission device information memory 16a, a reception device information memory 16b, and a memory 16c. The transmission device information memory 16a stores the data transmission waiting time from when the transmission device 11 receives the acknowledge signal until the data transmission is started. The reception device information memory 16b stores the intermittent reception interval of the reception device 12, the response signal transmission waiting time from when an actuation signal is received from the transmission device 11 until a response signal is sent, and the intermittent reception resumption waiting time from when the data transmission is completed until the intermittent reception is resumed. The memory 16c stores the time at which the acknowledge signal is received and the time at which intermittent reception is resumed by the reception device 12.

The blood glucose level measurement portion 17 electrically measures a blood glucose level when a measurement-use test piece is mounted in the blood glucose level measurement portion 17 and a spot of blood is placed on the test piece. The measured blood glucose level data is sent to the transmitter 13, and sent to the reception device 12 by wireless communication.

The constituent elements other than the blood glucose level measurement portion 17 will now be described in detail.

Figure 2:
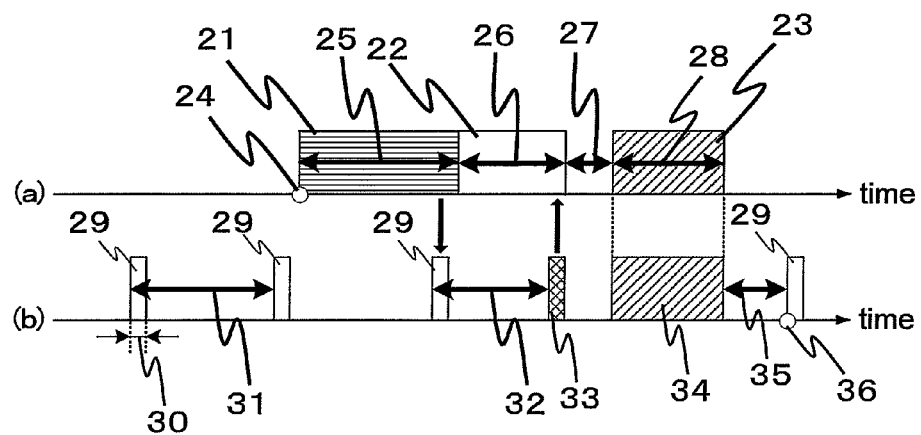
FIGS. 2a and 2b are timing charts for a transmission device and reception device the first time communication is performed.

First, we will describe the transmission device 11 through reference to FIGS. 2a and 2b. FIG. 2a is a timing chart for the transmission device 11 the first time communication is performed, while FIG. 2b is a timing chart for the reception device 12 the first time communication is performed. In FIGS. 2a and 2b, 21 is an actuation signal transmission operation, 22 is a response signal reception operation, 23 is a data transmission operation, 24 is a transmission start timing of actuation signal, 25 is a transmission duration of an actuation signal, 26 is a reception duration of a response signal, 27 is a data transmission waiting time (fixed) from acknowledge signal reception until the start of data transmission, 28 is a data transmission duration (variable according to data quantity), 29 is an intermittent reception operation in which reception is performed at regular intervals, 30 is an intermittent reception duration (regular intervals; fixed), 31 is an intermittent reception interval (regular intervals; fixed), 32 is a response signal transmission waiting time (fixed), 33 is a response signal transmission operation (an acknowledge signal in the example in FIGS. 2a and 2b), 34 is a data reception operation, 35 is the intermittent reception resumption waiting time (fixed) from completion of data communication until the resumption of the intermittent reception operation 29, and 36 is an intermittent reception timing.

The "first time communication is performed by the transmission device 11" here refers to the following situation.

Specifically, this is the first time the transmission device 11 is used, or when the battery that powers the transmission device 11 is replaced and the internal circuit is reset, or when the various parts of the transmission device 11 have been initially reset with a resetting switch provided to the transmission device 11, for example.

The transmission device 11 first performs the actuation signal transmission operation 21 when communication is commenced, and then performs the response signal reception operation 22 on the response signal, which is notification of the receipt of an actuation signal from the reception device 12. Upon receipt of an acknowledge signal, communication is established, and the data transmission operation 23 is performed. Here, the data sent in the data transmission operation 23 is blood glucose level information measured by the blood glucose level measurement portion 17. At this point the transmission duration 25 for the actuation signal transmission operation 21 is longer than the intermittent reception interval 31 that is the default.

If the response signal from the reception device 12 has not arrived during the period of the reception operation 22, or if there is a non-acknowledge signal indicating that the reception device 12 could not properly receive an actuation signal, the actuation signal transmission operation 21 is performed after the reception operation 22 in order to send the actuation signal again.

Figure 3:
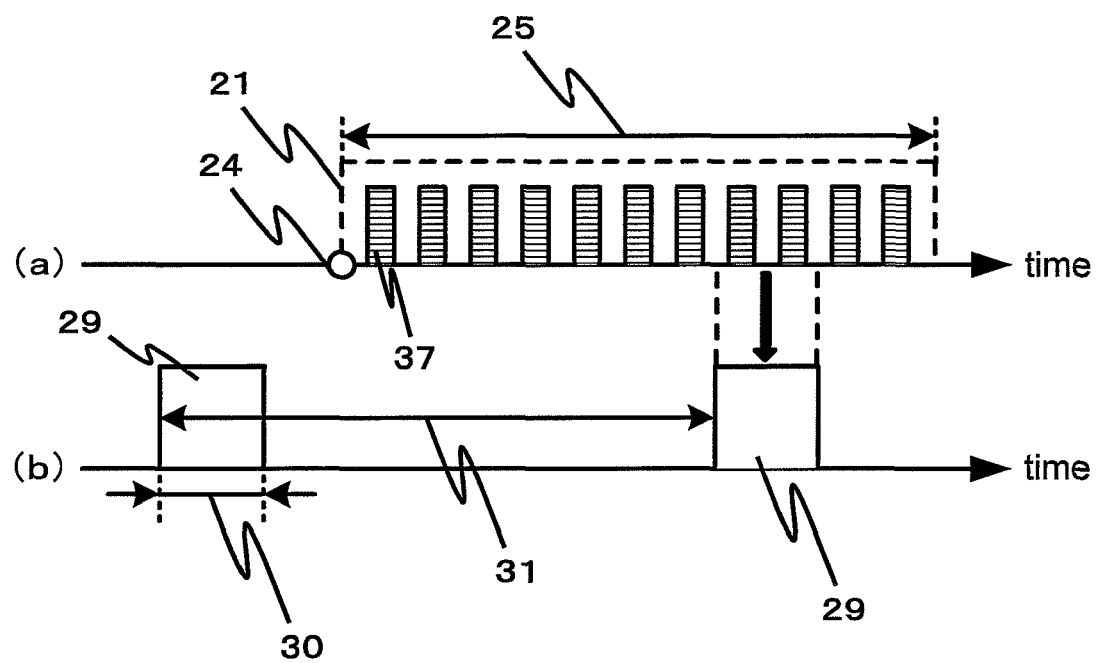
FIGS. 3a and 3b are timing charts for a transmission device and reception device during transmission and reception of an actuation signal.

Next, the internal constituent elements of the transmission device 11 will be described. First, we will describe the transmission/reception controller 14 through reference to FIGS. 3a and 3b. FIG. 3a is a timing chart in which the actuation signal transmission operation 21 of the transmission device 11 is expanded, and FIG. 3b is a timing chart in which the intermittent reception operation 29 of the reception device 12 is expanded. In FIGS. 3a and 3b, 37 is an actuation signal pulse that is send during the actuation signal transmission operation 21.

The transmission/reception controller 14 notifies the transmitter 13 of what is to be sent when communicating with the reception device 12 (an actuation signal or data), the transmission start timing 24 produced by the transmission condition determiner 14b, and the transmission duration 25 that is produced. Furthermore, the transmission/reception controller 14 notifies the reception specifier 16 of the data transmission duration 28 required to sent data. The transmitter 13 produces an actuation signal and performs the actuation signal transmission operation 21 according to the instruction from the transmission/reception controller 14. Also, the transmission/reception controller 14 stores the current time in the transmission time memory 14a in instructing the transmitter 13 to send an actuation signal. Here, for example, the actuation signal is the pulse 37 shown in FIG. 3a, which is sent repeatedly during the actuation signal transmission duration 25. The repetition period of this pulse 37 is at least a period in which the pulse 37 is included twice in the intermittent reception duration 30 of the reception device 12.

Information related to the time stored in the transmission time memory 14a is constituted so as to be erased when the above-mentioned resetting of the internal circuit is performed.

Upon being notified that an acknowledge signal has been received from the receiver 15, the transmission/reception controller 14 performs the data transmission operation 23 for sending data to the reception device 12 after the elapse of the data transmission waiting time 27.

During the first communication, the transmission condition determiner 14b sets the actuation signal transmission duration 25 to be longer than the intermittent reception interval 31 so that the reception device 12 can receive an actuation signal (the same as the actuation signal transmission duration 25 shown in FIGS. 2a and 2b).

During the second and subsequent times communication is performed, the transmission start timing of the actuation signal 24 and the actuation signal transmission duration 25 are decided on the basis of the transmission start time of the previous iteration stored in the transmission time memory 14a, the acknowledge signal reception time (discussed below), and the intermittent reception timing 36 of the reception device 12 outputted by the reception specifier 16.

Figure 4:
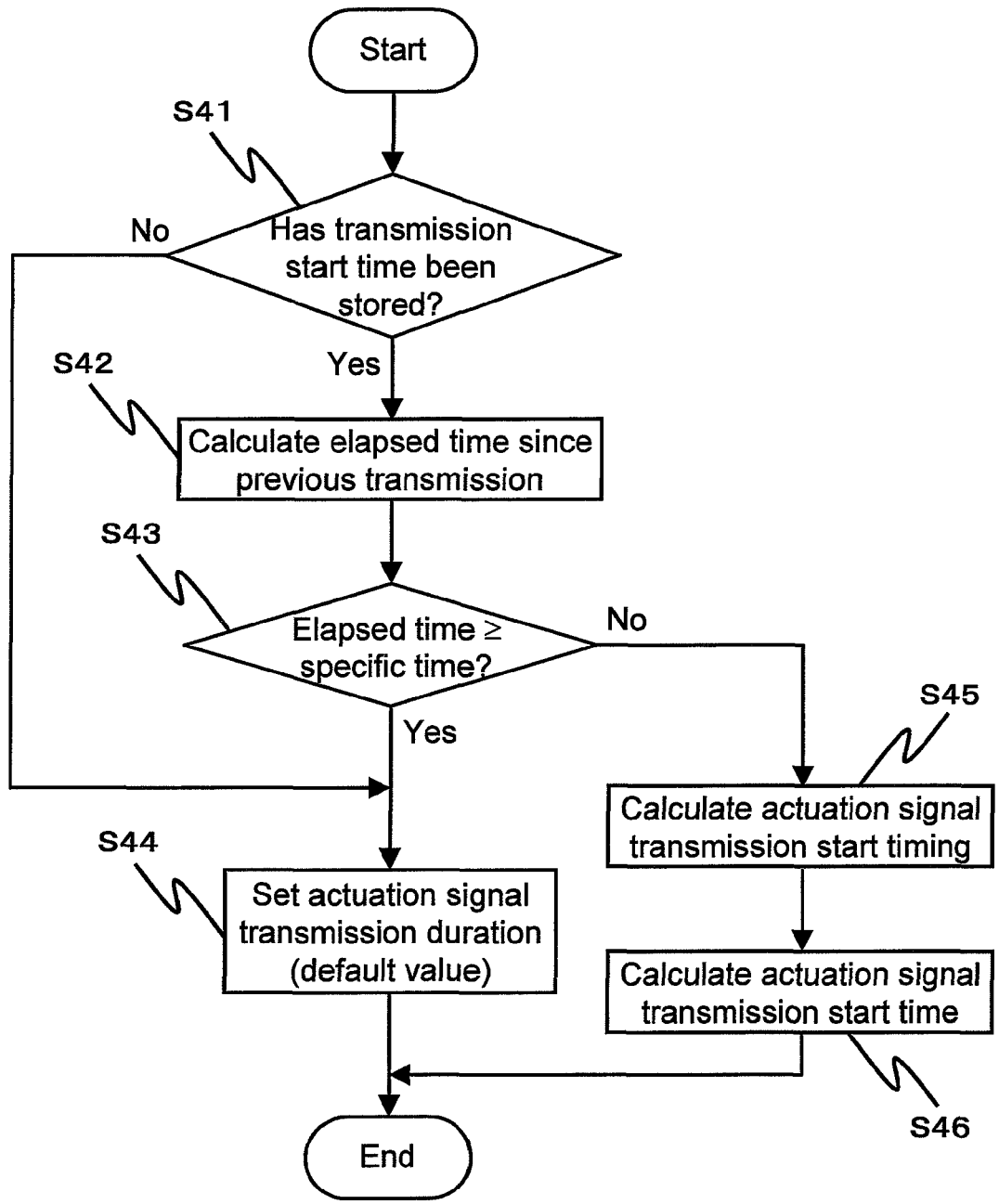
FIG. 4 is a decision processing flowchart of the transmission start timing and transmission duration for an actuation signal with the transmission/reception controller.
Figure 5:
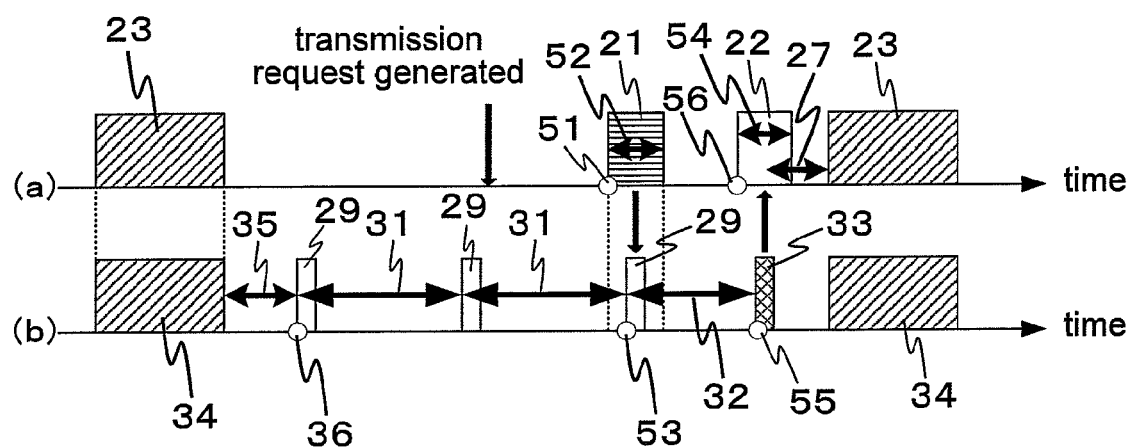
FIGS. 5a and 5b are timing charts for a transmission device and reception device the second and subsequent times communication is performed.

Processing for determining the transmission start timing of the actuation signal 24 and the actuation signal transmission duration 25 performed by the transmission condition determiner 14b will now be described through reference to FIGS. 4, 5a, and 5b. FIG. 4 is a flowchart of the processing performed by the transmission condition determiner 14b for determining the transmission start timing of the actuation signal 24 and the actuation signal transmission duration 25. FIG. 5a is a timing chart for the transmission device 11 the second and subsequent times communication is performed, while FIG. 5b is a timing chart for the reception device 12 the second and subsequent times communication is performed.

FIGS. 5a and 5b show the situation up until the next transmission request is generated after the transmission device 11 and the reception device 12 have completed their first data communication (the data transmission operation 23 and the data reception operation 34), until the end of the second data communication. In FIGS. 5a and 5b, 51 is an actuation signal transmission start timing for the second data communication, 52 is an actuation signal transmission duration for the second data communication, 53 is an intermittent reception timing closest to the timing at which a transmission request is generated, 54 is a response signal reception duration, 55 is a response signal transmission start timing, and 56 is a response signal reception start timing.

The operation of the transmission condition determiner 14b will now be described.

When a transmission request is generated at the timing shown in FIG. 5a, the transmission condition determiner 14b checks whether or not the transmission start time for the previous iteration has been stored in the transmission time memory 14a (step S41).

Next, if the transmission start time for the previous iteration has been stored in the transmission time memory 14a, the transmission condition determiner 14b reads this and calculates the elapsed time from the previous transmission start time until the generation of a transmission request (step S42).

In step S42, the transmission condition determiner 14b checks whether or not the calculates elapsed time is more than a specific length of time (such as 24 hours) (step S43).

In step S41, if the previous transmission start time has not been stored in the transmission time memory 14a, or if the elapsed time from the previous transmission start time in step S43 until the generation of a transmission request is equal to or greater than a specific length of time, the transmission condition determiner 14b sets the actuation signal transmission duration to the default value. The default value is set (for example, 15 seconds when the intermittent reception interval is 10 seconds) so that the transmission duration will be longer than the intermittent reception interval 31, so that the actuation signal can be properly received by the reception device 12 (step S44). There are no particular restrictions on the actuation signal transmission start timing here, and any timing at all may be used.

Meanwhile, if the previous transmission start time has been stored in the transmission time memory 14a, and the elapsed time from the previous transmission start time in step S43 until the generation of a transmission request is less than a specific length of time, then the transmission condition determiner 14b utilizes the intermittent reception interval 31 and the intermittent reception timing 36 of the reception device 12 specified by the reception specifier 16 (discussed below) according to the elapsed time, and calculates the actuation signal transmission start timing 51 and the actuation signal transmission duration 52. Here, if the transmission request is generated at the timing shown in FIG. 5a, the transmission condition determiner 14b calculates the timing 53 closest to the current time at a timing that is an integer multiple of the intermittent reception interval 31 from the intermittent reception timing 36 (the intermittent reception resumption time discussed below). This timing 53 is the timing at which the reception device 12 performs the intermittent reception operation 29 the closest to the timing at which the transmission request is generated. Accordingly, clock error of the transmission device 11 and the reception device 12 is taken into account, and the transmission condition determiner 14b determines the actuation signal transmission start timing 51 and the actuation signal transmission duration 52 so as to reliably cover the intermittent reception duration 30 from the timing 53.

For example, if the elapsed time from the previous transmission start time is less than 10 times the intermittent reception interval 31, the transmission condition determiner 14b matches the actuation signal transmission duration 52 to the next intermittent reception timing 53, and sets the actuation signal transmission start timing 51 to the same length as the intermittent reception duration 30. On the other hand, if the elapsed time from the previous transmission start time is greater than or equal to 10 times the intermittent reception interval 31, the transmission condition determiner 14b sets the actuation signal transmission start timing 51 earlier than the intermittent reception timing 53 and sets the actuation signal transmission duration 52 to be longer than the intermittent reception duration 30 so that the actuation signal transmission duration 52 will cover the intermittent reception duration 30.

The transmission condition determiner 14b determines the actuation signal transmission start timing 51 so that it will be earlier than the intermittent reception timing 53 in proportion to the elapsed time since the previous communication start time. The transmission condition determiner 14b also sets the actuation signal transmission duration 52 so that it is longer in proportion to the elapsed time since the previous communication start time, and will at most be the default value. Consequently, proper communication will still be possible even if the timing should be offset due to clock error (steps S45 and S46).

After this, when the actuation signal transmission operation 21 ends, the transmission/reception controller 14 instructs the receiver 15 to perform the response signal reception operation 22 under the conditions set by the reception condition determiner 14c. During the above-mentioned first communication, the transmission/reception controller 14 sets the response signal reception duration 54 longer than the response signal transmission waiting time 32 immediately after the actuation signal transmission operation 21, so that the transmission device 11 will be able to receive a response signal.

Meanwhile, during the second and subsequent times communication is performed, the transmission condition determiner 14b calculates the intermittent reception timing 53 that is closest after the generation of the transmission request. Accordingly, the reception condition determiner 14c can use this information to calculate the response signal transmission start timing 55 at which the reception device 12 starts the response signal transmission operation 33, on the basis of the intermittent reception timing 53 and the response signal transmission waiting time 32. The reception condition determiner 14c sets the response signal reception duration 54 and the start timing 56 for the response signal reception operation 22 so as to cover the response signal transmission operation 33 of the reception device 12. Consequently, the response signal reception duration 54 of the response signal reception operation 22 of the transmission device 11 can be shortened.

Next, the operation of the receiver 15 will be described.

The receiver 15 performs the response signal reception operation 22 at an instruction from the transmission/reception controller 14. When the actuation signal transmission operation 21 is complete, the transmission/reception controller 14 instructs the receiver 15 to perform the response signal reception operation 22. Upon receiving a response signal from the reception device 12 after the start of the response signal reception operation 22, the receiver 15 determines whether or not it is an acknowledge signal. If the received response signal is an acknowledge signal, the transmission/reception controller 14 and the reception specifier 16 are notified that an acknowledge signal has been received. If the received response signal cannot be identified, on the other hand, it is ignored, and the response signal reception operation 22 is continued until a specific length of time has passed. If a response signal cannot be received even after this specific time has passed, or if the received response signal is a non-acknowledge signal, the transmission/reception controller 14 is notified to perform the retransmission of an actuation signal.

Next, the operation of the reception specifier 16 will be described through reference to FIGS. 2a, 2b, 5a, and 5b.

The reception specifier 16 has a transmission device information memory 16a, a reception device information memory 16b, and a memory 16c. The transmission device information memory 16a stores the data transmission waiting time 27 from when the acknowledge signal is received by the transmission device 11 until data transmission begins. The reception device information memory 16b stores the intermittent reception interval 31 of the reception device 12, the response signal transmission waiting time 32 from when the actuation signal is received from the transmission device 11 until the response signal is sent, and the intermittent reception resumption waiting time 35 from the end of communication until the intermittent reception operation 29 is resumed. The memory 16c stores the current time as the acknowledge signal reception time upon being notified that an acknowledge signal has been received from the receiver 15. The reception specifier 16 specifies the intermittent reception timing 36 of the reception device 12 on the basis of the acknowledge signal reception time, the data transmission waiting time 27, the data transmission duration 28, and the intermittent reception resumption waiting time 35, and stores this as the intermittent reception resumption time in the memory 16c.

Next, the operation of the reception device 12 will be described through reference to FIGS. 2a, 2b, 5a, and 5b.

The reception device 12 performs the intermittent reception operation 29 until the start of communication, and when an actuation signal is received from the transmission device 11, the reception device 12 waits through the response signal transmission waiting time 32, and then performs the response signal transmission operation 33 on the transmission device 11 at the response signal transmission start timing 55. Here, the response signal transmission waiting time 32 is set shorter than the intermittent reception interval 31, and is set so that after the actuation signal is received from the transmission device 11, the response signal will be sent to the transmission device 11 by the next intermittent reception operation 29.

After this, the reception device 12 waits for a transmission start request from the transmission device 11, and once a transmission start request has been received from the transmission device 11, the data reception operation 34 is started. If a communication end request has been received from the transmission device 11, the reception device 12 ends the data reception operation 34 and waits through the intermittent reception resumption waiting time 35, after which the intermittent reception operation 29 is resumed from the intermittent reception timing 36 shown in FIG. 2b (the intermittent reception resumption time). If a signal received from the transmission device 11 cannot be identified as being an actuation signal, a non-acknowledge signal is sent to the transmission device 11 in the response signal transmission operation 33, and the intermittent reception operation 29 is continued.

Figure 6:
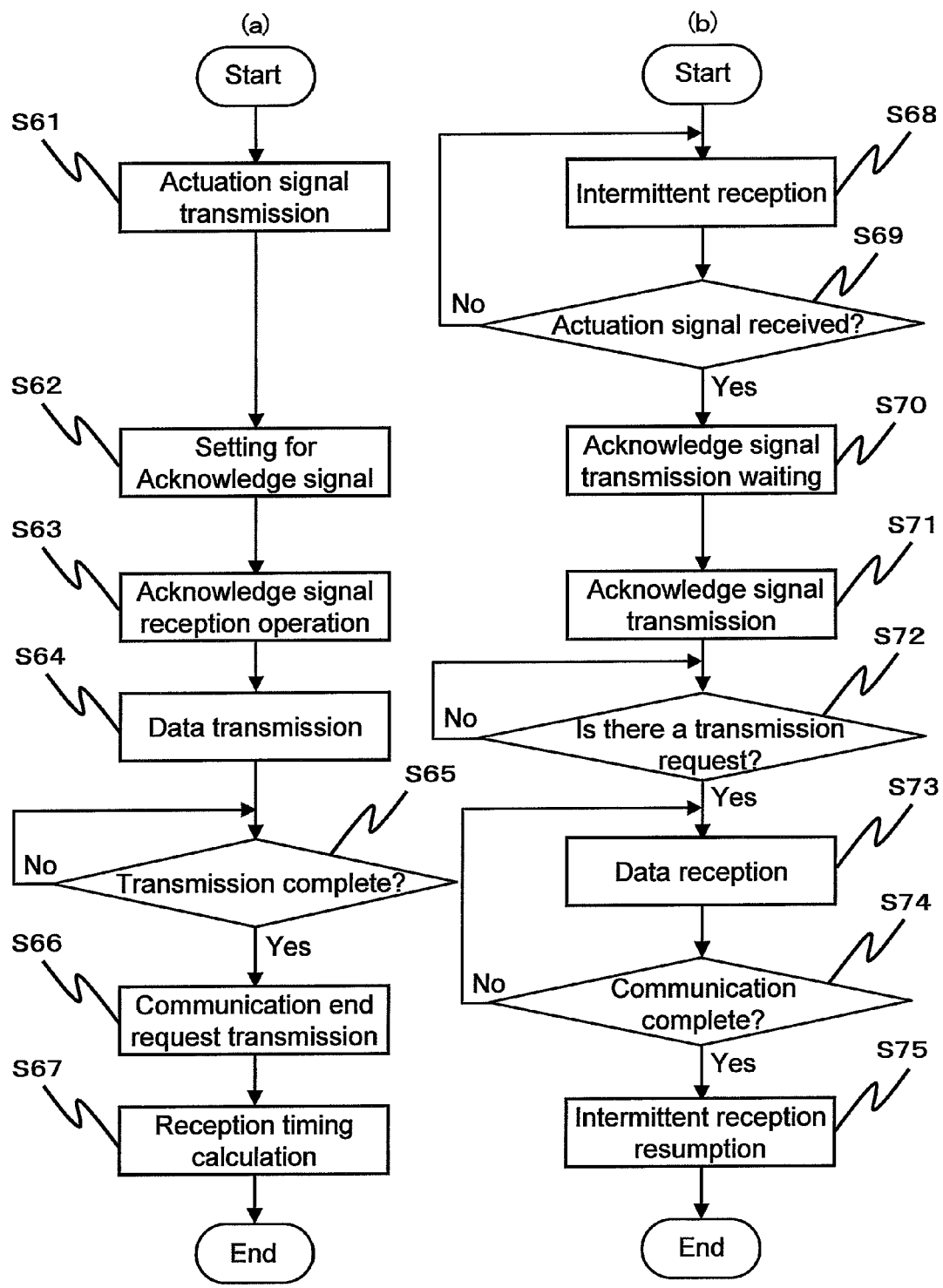
FIGS. 6a and 6b are communication processing flowcharts of the transmission device and reception device in Embodiment 1.
Figure 7:
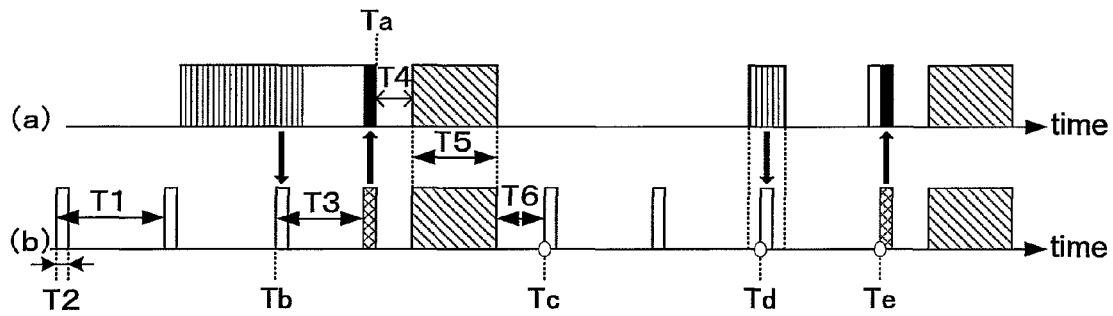
FIGS. 7a and 7b are communication processing timing charts of the transmission device and reception device in Embodiment 1.

Next, the communication operation of the transmission device 11 and the reception device 12 in an embodiment of the present invention will be described through reference to FIGS. 6a, 6b, 7a, and 7b. FIG. 6a is a flowchart of the transmission device 11, FIG. 6b is a flowchart of the reception device 12, FIG. 7a is a timing chart of the transmission device 11, and FIG. 7b is a timing chart of the reception device 12.

First the operation of the transmission device 11 will be described.

With the transmission device 11, when communication begins, the transmission/reception controller 14 instructs the transmitter 13 to sent an actuation signal to the reception device 12. Here the transmission condition determiner 14b uses the intermittent reception resumption time stored in the memory 16c and the elapsed time from the previous transmission start time stored in the transmission time memory 14a to calculate the actuation signal transmission start timing and the transmission duration. The specific method for calculating the actuation signal transmission start timing and the transmission duration was already described in regard to the operation of the transmission/reception controller 14, and so will not be described again here (step S61).

With the transmission device 11, after the actuation signal has been sent, the transmission/reception controller 14 instructs the receiver 15 to perform the response signal reception operation 22 so as to receive an acknowledge signal that is a notification of the reception the actuation signal by the reception device 12. Here, the reception condition determiner 14c calculates the response signal reception duration 54 and the start timing 51 of the response signal reception operation 22 according to the elapsed time since the previous transmission start time stored in the transmission time memory 14a. The specific method for calculating the response signal reception duration 54 and the start timing 51 of the response signal reception operation 22 was already described in regard to the operation of the transmission/reception controller 14, and so will not be described again here (step S62).

The receiver 15 performs the response signal reception operation 22 under the conditions specified by the transmission/reception controller 14. This reception operation is continued until either a response signal is received or a specific amount of time has elapsed. If the response signal received by the receiver 15 is an acknowledge signal, the receiver 15 notifies the transmission/reception controller 14 and the reception specifier 16 that an acknowledge signal has been received (this timing shall be referred to as the acknowledge signal reception timing Ta). On the other hand, if a specific amount of time has elapsed without an acknowledge signal being received, the receiver 15 notifies the transmission/reception controller 14 to resend. Although not depicted in the drawings, the flow returns to step S61 here (step S63).

The transmission/reception controller 14 sends a data transmission request to the reception device 12 and starts data transmission once a data transmission waiting time T4 has elapsed since the acknowledge signal reception timing Ta (step S64).

The transmission/reception controller 14 checks whether or not the data has been transmitted all the way to the end, and if the data transmission has not been completed to the end, the data transmission operation is continued (step S65).

On the other hand, if the data transmission has been completed to the end, the transmission/reception controller 14 sends a communication end request to the reception device 12 and ends the processing, and notifies the reception specifier 16 (step S66).

The reception specifier 16 specifies the intermittent reception timing Tc of the reception device 12 by using the data transmission waiting time T4 from the acknowledge signal reception timing Ta of the transmission device 11 stored in the memory 16c (the acknowledge signal reception time), the intermittent reception resumption waiting time T6 from the completion of communication stored in the reception device information memory 16b until intermittent reception is resumed, and the data transmission time T5 indicated by the transmission/reception controller 14. The reception specifier 16 stores the specified intermittent reception timing Tc of the reception device 12 in the memory 16c as the intermittent reception resumption time (step S67).

At this point the reception timing Tc is the sum of adding T4, T5, and T6 to Ta. Subsequent reception timing becomes Tc+T1, Tc+2×T1, Tc+3×T1, . . . Tc+n×T1 (where n is a natural number).

The operation of the reception device 12 will now be described.

The reception device 12 first starts the intermittent reception operation 29 in which reception is repeated for a period of T2 at specific intervals T1, and awaits an actuation signal from the transmission device 11 that will trigger the start of communication (step S68).

The reception device 12 checks whether or not the actuation signal sent from the transmission device 11 has been received during the reception operation. If no actuation signal has been received here, the flow returns to step S68, and the intermittent reception operation 29 is continued (step S69).

On the other hand, if an actuation signal has been received by the reception device 12, the system waits for a response signal transmission waiting time T3 until the acknowledge signal that is a notification of reception of the actuation signal is sent to the transmission device 11 (step S70).

At the end of the response signal transmission waiting time T3, the reception device 12 performs the acknowledge signal transmission operation 33 with respect to the transmission device 11 (step S71).

After the acknowledge signal has been sent, the reception device 12 begins a data transmission request reception operation, and checks whether or not a data transmission request has been received from the transmission device 11. If no data transmission request has been received, the data transmission request reception operation is continued (step S72).

Meanwhile, if a data transmission request has been received in step S72, the data reception operation 34 is begun (step S73).

The reception device 12 checks whether or not a communication end request has been received from the transmission device 11. If no communication end request has been received here, the flow returns to step S73 and the data reception operation 34 is continued (step S74).

On the other hand, if a communication end request has been received in step S74, the data reception operation 34 is ended, and the intermittent reception operation 29 is resumed after the intermittent reception resumption waiting time T6 has elapsed (step S75).

As discussed above, in Embodiment 1, the transmission device 11 can send an actuation signal that matches the timing of the intermittent reception operation of the reception device 12. Thus, the actuation signal transmission duration can be shortened, and the power consumption of the transmission device 11 can be reduced.

Furthermore, since communication is controlled so that the transmission duration is lengthened according to how much time has elapsed since the previous communication, communication can be carried out properly even if offset of the times mutually recognized by the transmission device and the reception device increases a little at a time due to internal clock error.

Embodiment 2

In Embodiment 1 above, an example was given in which a data communication operation was performed after an actuation signal was sent from the transmission device 11 and communication was established at the start of communication. In this Embodiment 2, an example is given of a wireless communication apparatus in which the amount of data being communicated is smaller, and communication establishment and data transmission are carried out simultaneously. Specifically, this embodiment is different in that data is sent instead of the actuation signal sent in Embodiment 1 above.

Figure 8:
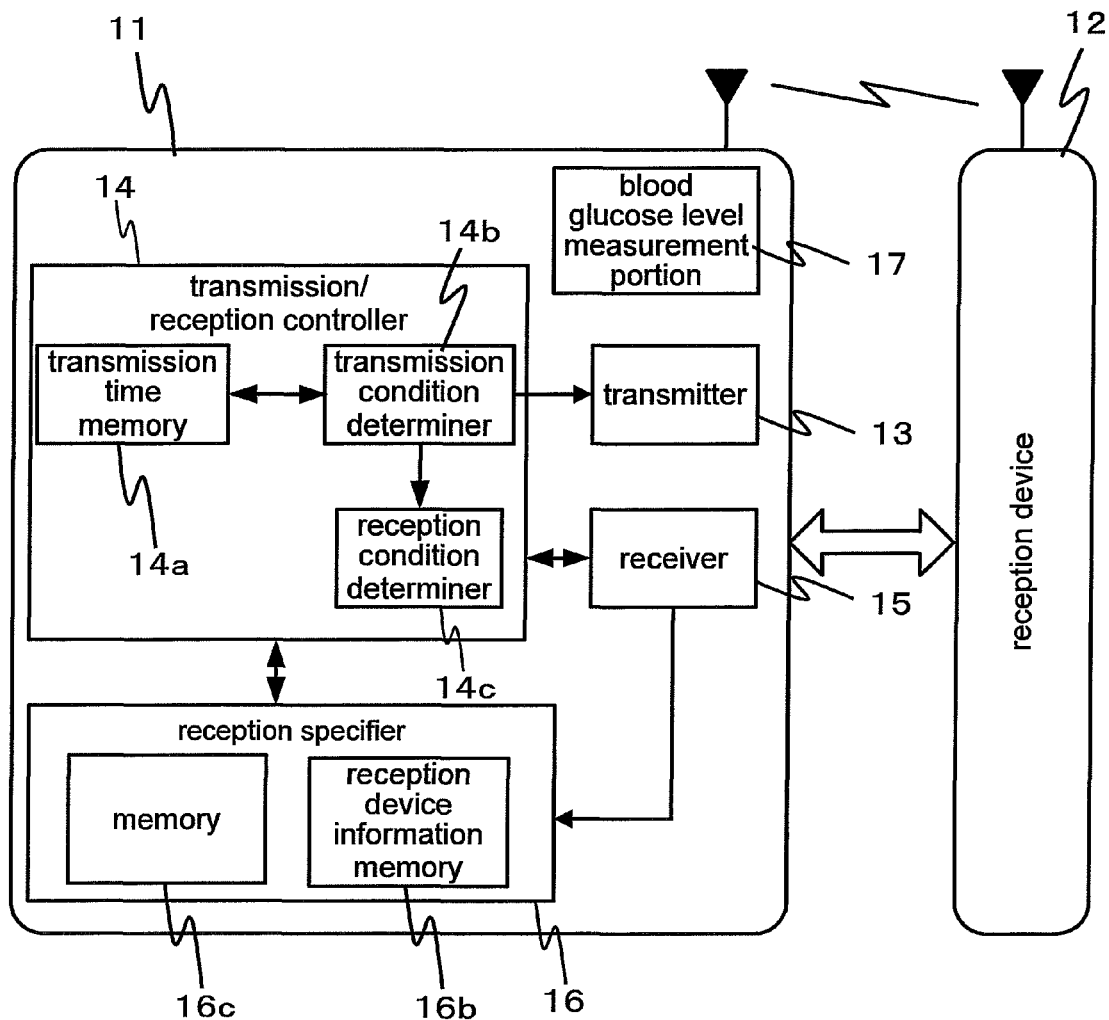
FIG. 8 is a diagram of the configuration of a wireless communication apparatus in Embodiment 2.
Figure 9:
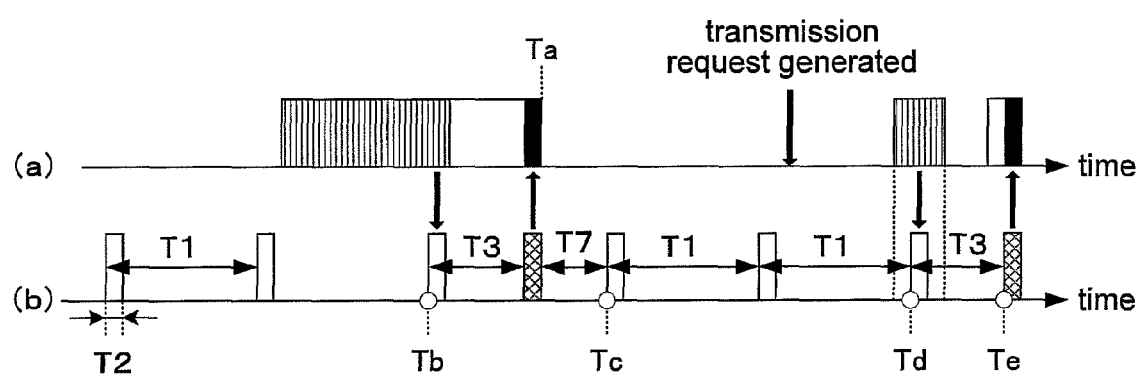
FIGS. 9a and 9b are communication processing timing charts of the transmission device and reception device in Embodiment 2.

FIG. 8 is a diagram of the configuration of the wireless communication apparatus in Embodiment 2, and FIGS. 9a and 9b are timing charts for the communication processing between the transmission device 11 and the reception device 12 in this Embodiment 2. FIG. 9a is a timing chart for the transmission device 11, while FIG. 9b is a timing chart for the reception device 12.

In FIG. 8, what is different from the wireless communication apparatus in Embodiment 1 as illustrated in FIG. 1 is that there is no transmission device information memory 16a within the reception specifier 16. Also, since the reception device 12 receives data without interrupting the intermittent reception, only the response signal transmission waiting time 32 is stored in the reception device information memory 16b.

Just as in Embodiment 1 above, the transmission/reception controller 14 stores the time at which the data was sent, instead of an actuation signal, in the transmission time memory 14a.

Furthermore, the processing performed by the reception specifier 16 in specifying the intermittent reception time immediately after the data was sent from the transmission device 11 to the reception device 12 (the intermittent reception resumption time in Embodiment 1) is changed as follows.

First, if the response signal received from the reception device 12 is an acknowledge signal, the reception specifier 16 stores this time (the acknowledge signal reception time) in the memory 16c. Next, the intermittent reception time that immediately follows is found by calculating {the acknowledge signal reception time+(the intermittent reception interval−the response signal transmission waiting time)}, and this is stored as the immediately following intermittent reception time in the memory 16c.

The transmission/reception controller 14 then determines the timing at which the data will be sent, just as in Embodiment 1 above. Specifically, the timing closest to the current time, and which is an integer multiple of the intermittent reception interval from the calculated intermittent reception time stored in the memory 16c and calculated when a data transmission request was generated, is specified as the timing of the data transmission. The fact that the transmission timing and the transmission duration are corrected according to the time elapsed since the previous data transmission time is the same as in the processing described for Embodiment 1 above.

The operation of the wireless communication apparatus in Embodiment 2 will now be described through reference to FIGS. 9a and 9b.

First, the operation of the transmission device 11 will be described.

When communication is begun, the transmission device 11 notifies the transmitter 13 of the conditions specified by the transmission condition determiner 14b in order to perform data transmission with respect to the reception device 12. Here, the transmission condition determiner 14b calculates the data transmission start timing and the transmission duration according to the time elapsed since the previous transmission start time stored in the transmission time memory 14a. During the first communication, the time is set longer than the intermittent reception interval T1 of the reception device 12. When communication is performed for the second and subsequent times, however, the intermittent reception interval T1 and the intermittent reception timing Tc outputted by the reception specifier 16 are utilized to calculate the intermittent reception timing Td closest to the time when the transmission request was generated, and sets the transmission start timing and the transmission duration so as to cover the intermittent reception duration T2.

With the transmission device 11, after data transmission, the transmission/reception controller 14 instructs the receiver 15 to perform a response signal reception operation under the conditions specified by the reception condition determiner 14c in order to receive an acknowledge signal that is a notification that data has been received by the reception device 12. Here, the reception condition determiner 14c calculates the start timing for the response signal reception operation and the reception duration according to how much time has elapsed since the previous transmission start timing stored in the transmission time memory 14a. During the first communication, the period is set longer than the response signal transmission waiting time T3. On the other hand, when communication is performed the second and subsequent times, the response signal transmission waiting time T3, the intermittent reception interval T1, and the intermittent reception timing Tc outputted by the reception specifier 16 are utilized to calculate the intermittent reception timing Td closest to the time when the transmission request was generated, and then calculates the response signal transmission start timing Te. The response signal reception duration of the transmission device 11 is set so as to cover the response signal transmission duration.

The transmission device 11 checks whether or not the receiver 15 has received a response signal from the reception device 12. If no response signal has been received by the receiver 15, the response signal reception operation is repeated until a specific amount of time has passed. On the other hand, if an acknowledge signal has been received by the receiver 15, the receiver 15 notifies the transmission/reception controller 14 and the reception specifier 16 that an acknowledge signal has been received. If the received response signal here is a non-acknowledge signal, the transmission/reception controller 14 is immediately notified to resend the data, without waiting for the end of the response signal reception duration.

The reception specifier 16 specifies the intermittent reception timing Tc for the reception device 12 from the time T7 until the next intermittent reception operation on the basis of the acknowledge signal transmission timing of the reception device 12 and the acknowledge signal reception timing Ta of the transmission device 11. The time T7 here is obtained by subtracting the response signal transmission waiting time T3 from the intermittent reception interval T1. The reception specifier 16 stores the intermittent reception timing Tc of the reception device 12 in the memory 16c.

The operation of the reception device 12 will now be described.

The reception device 12 first starts the intermittent reception operation 29 in which reception is repeated for a time of T2 at the specific interval T1, and awaits the transmission of data from the transmission device 11.

Next, the reception device 12 checks whether or not the data sent from the transmission device 11 during the reception operation has been received, and if the data has not been received, the intermittent reception operation 29 is continued.

On the other hand, if the reception device 12 has received the data, it waits for the response signal transmission waiting time T3 until an acknowledge signal that is a data reception notification is sent to the transmission device 11.

When the waiting for the response signal transmission waiting time T3 is over, the reception device 12 performs the acknowledge signal transmission operation 33 with respect to the transmission device 11.

Upon completion of the acknowledge signal transmission operation 33, the reception device 12 resumes the intermittent reception operation 29 after waiting for the time T7.

As discussed above, in this Embodiment 2, the transmission device 11 sends the data that matches the timing of the intermittent reception operation of the reception device 12, and the reception operation is matched to the response signal transmission operation of the reception device. Consequently, the transmission and reception durations can be shortened, and the power consumption of the transmission device 11 can be reduced.

The transmission device pertaining to the present invention, and the wireless communication apparatus in which this transmission device is used, allow the transmission duration of the transmission device to be shortened and the power consumption to be reduced, and are therefore useful as a mobile health care system or the like.

The invention claimed is:

1. A transmission device for performing communication with a reception device that performs intermittent reception, comprising:
    a transmitter configured to transmit various signals to the reception device;
    a receiver configured to receive a response signal emitted from the reception device in response to a transmission of the various signals from the transmitter to the reception device;
    a reception specifier configured to specify a reception timing of an intermittent reception of the reception device when a response signal from the reception device has been received; and
    a transmission/reception controller configured to perform control of the receiver and the transmitter, and decide a timing at which the transmission of the various signals will begin, and how long the transmission will last, on the basis of the reception timing specified by the reception specifier,
    wherein the transmission/reception controller has a transmission condition determiner configured to determine a transmission duration and a timing at which transmission begins for an actuation signal included in the various signals, and a transmission time memory configured to store a time at which a latest transmission was completed, and
    the transmission condition determiner changes the transmission duration and the timing at which the transmission of the various signals began according to a time that has elapsed since the latest transmission time was stored in the transmission time memory.

2. The transmission device according to claim 1, further comprising:
    a transmission device information memory configured to store a data transmission waiting time from when the response signal is received until a data transmission begins; and
    a reception device information memory configured to store an intermittent reception interval of the reception device, a response signal transmission waiting time from when the various signals are received until the response signal is transmitted, and an intermittent reception resumption waiting time from the end of communication until intermittent reception is resumed,
    wherein the reception specifier specifies the reception timing of an intermittent reception of the reception device on the basis of the timing at which the response signals are received, the data transmission waiting time, and the intermittent reception resumption waiting time.

3. The transmission device according to claim 2, wherein the transmission/reception controller has a transmission condition determiner configured to determine a transmission duration and a timing at which transmission begins for an actuation signal included in the various signals, and a transmission time memory configured to store the time at which the latest transmission was made, and
    the transmission condition determiner changes the transmission duration and the timing at which the transmission of the various signals began according to the time elapsed since the latest transmission time stored in the transmission time memory.

4. The transmission device according to claim 1, further comprising:
    a reception device information memory configured to store an intermittent reception interval of the reception device and a response signal transmission waiting time from when the various signals are received until the response signal is transmitted,
    wherein the reception specifier specifies the reception timing of an intermittent reception of the reception device on the basis of the reception timing of the response signal.

5. The transmission device according to claim 4, wherein the transmission/reception controller has a transmission condition determiner configured to determine a transmission duration and a timing at which transmission begins for an actuation signal included in the various signals, and a transmission time memory configured to store the time at which the latest transmission was made, and
    the transmission condition determiner changes the transmission duration and the timing at which the transmission of the various signals began according to the time elapsed since the latest transmission time stored in the transmission time memory.

6. A wireless communication apparatus having a reception device that performs intermittent reception and a transmitting device for performing communication with the reception device, comprising:
    the transmission device including:
    a transmitter configured to transmit various signals to the reception device;
    a receiver configured to receive a response signal emitted from the reception device in response to a transmission of the various signals from the transmitter to the reception device;
    a reception specifier configured to specify a reception timing of an intermittent reception of the reception device when a response signal from the reception device has been received;
    a transmission/reception controller configured to perform control of the receiver and the transmitter, and decide a timing at which the transmission of the various signals will begin, and how long the transmission will last, on the basis of the reception timing specified by the reception specifier; and a reception device configured to send a response signal to the transmission device upon properly receiving the various signals transmitted from the transmission device, wherein the transmission/reception controller has a transmission condition determiner configured to determine a transmission duration and a timing at which transmission begins for an actuation signal included in the various signals, and a transmission time memory configured to store a time at which a latest transmission was completed; and the transmission condition determiner changes the transmission duration and the timing at which the transmission of the various signals began according to a time that has elapsed since the latest transmission time was stored in the transmission time memory.

7. The wireless communication apparatus according to claim 6,
wherein the transmission device sends a data obtained by measuring a blood glucose level to the reception device.

8. The wireless communication apparatus according to claim 7,
wherein the reception device is a portable information terminal.

9. The wireless communication apparatus according to claim 6,
wherein the reception device is a portable information terminal.

* * * * *